United States Patent [19]

Mukkala et al.

[11] Patent Number: 5,457,186
[45] Date of Patent: Oct. 10, 1995

[54] LUMINESCENT LANTHANIDE CHELATES WITH DECREASED NON-RADIATIVE ENERGY LOSS

[75] Inventors: Veli-Matti Mukkala, Kaarina; Harri Takalo, Turku; Ilkka Hemmilä, Kaarina; Jouko Kankare, Turku, all of Finland

[73] Assignee: Wallac Oy, Turku, Finland

[21] Appl. No.: 135,525

[22] Filed: Oct. 13, 1993

[51] Int. Cl.[6] .............................. C07F 5/00; C09K 11/06
[52] U.S. Cl. ..................... 534/15; 252/301.18; 534/16
[58] Field of Search .................. 534/15, 16; 252/301.18; 424/1.81

[56] References Cited

U.S. PATENT DOCUMENTS 3,451,009  6/1969  Ross .
3,466,568  9/1969  Heller .

OTHER PUBLICATIONS

CA 83:199669; Sveshnikova et al, Opt. Spektrosk (1975) 39(2), 285–289.
CA 88:113069; Goryaeva et al., Zh. Prikl. Spektrosk. (1978), 28(1), 75–80.

*Primary Examiner*—Philip Tucker
*Attorney, Agent, or Firm*—Ronald J. Kubovcik

[57] ABSTRACT

A method of conducting assays for analytes, usually from biological samples, utilizing bioaffinity reagents linked to luminescent lanthanide chelates, which are synthesized so that the non-radiative quenching of the ion luminescence through C—H bond vibrational energy manifolds is avoided using a stable chelate where the CH and $CH_2$ groups in the vicinity of the emittive ion are substituted with CD and $CD_2$ groups hence producing improved luminescence quantum yield and higher assay sensitivities.

10 Claims, 1 Drawing Sheet

FIG. 1

LUMINESCENT LANTHANIDE CHELATES WITH DECREASED NON-RADIATIVE ENERGY LOSS

FIELD OF THE INVENTION

The present invention relates to novel highly luminescent lanthanide chelates and a method for their preparation. The invention further relates to novel detectable molecules comprising said lanthanide chelates attached to a biospecific binding reactant. The invention further relates to novel chelating agents useful in the preparation of said chelates.

BACKGROUND OF THE INVENTION

The publications and other materials used herein to illuminate the background of the invention, and in particular, cases to provide additional details respecting the practice, are incorporated by reference.

In the specific binding assays, such as e.g. immunoassays, DNA hybridization assays, receptor-binding assays, and cellular binding assays, generally the analytes to be measured are present at very low concentrations. Therefore various labelling compounds have been developed that allow the labelled reactant to be detected and quantitated at a high sensitivity. Originally, radioisotopic labels were solely used, but recently, because of the limitations of those labels (such as limited shelf life, safety, health and waste problems and so on) a number of non-radioactive alternatives have been introduced. Fluorometry is a versatile label technology found wide applications in a number of analytical assays based on bioaffinity reactions, such as in situ hybridization, immunohisto and cytochemistry, and also in quantitative fluoroimmunoassays. Although theoretically very sensitive, fluorometric determination is very vulnerable to interferences caused by background sources (Soini, E. and Hemmilä, I., 1979, Clin Chem 25; 353 ).

Application of delayed detection of fluorescence excited with a short pulse is a frequently used system to avoid background problems by taking advantage of the temporal separation of specific fluorescence from unspecific background interference of shorter decay-time (Hemmilä, I., 1991, Applications of Fluorescence in Immunoassays, Wiley, New York). The system requires, however, a photoluminescent (referred in the context of this text simply as luminescent) label having an excited state lifetime clearly longer than the average background noise. Therefore, the research is focused in developing luminescent lanthanide chelates, which because of the electronic structure of the ions, have unique luminescence properties including exceptionally long decay times ranging from microseconds to milliseconds. A system based on two different chelates, one optimized for labelling and the other for fluorometric determination, DELFIA® (trademark of Wallac) (U.S. Pat. No. 4,565,790, U.S. Pat. No. 4,808,541) has found established applications particularly in clinical diagnostics. Because of the dissociation step required, this system does not, however, suit for analysis where spatial information is also needed, e.g. for in situ immunofluorescence staining, or in situ hybridizations, neither for multianalyte assays based of distinct solid-phases. Therefore, a number of attempts have been made to develop new highly luminescent chelate labels suitable for those types of time-resolved fluorometric applications. These include e.g. stable chelates composed of derivatives of pyridines (U.S. Pat. No. 4,920,195, U.S. Pat. No. 4,801,722, U.S. Pat. No. 4,761,481, PCT WO FI-91/00373), bipyridines (U.S. Pat. No. 5,216,134), terpyridines (U.S. Pat. No. 4,859,777, U.S. Pat. No. 5,202,423) or various phenolic compounds (U.S. Pat. No. 4,670,572, U.S. Pat. No. 4,794,191) as the energy mediating groups and polycarboxylic acids as chelating parts. In addition various dicarboxylate derivatives (U.S. Pat. No. 5,032,677, U.S. Pat. No. 5,055,578, U.S. Pat. No. 4,772,563), macrocyclic cryptates (U.S. Pat. No. 4,927,923, PCT WO 93/5049, EP-A 493,745) and macrocyclic Schiff bases (EP-A 369,000) have been patented. The problem still existing with all these compounds relates to the relatively low quantum yield, generally decays apart from the optimum (100%) level. Regardless of employment of very stable chelates, such as the cage-type cryptates or nine-dentate terpyridine derivatives, there still remains problems of non-radiative quenching, especially profound with the positively charged cryptates caused by anionic compounds derived from biological samples (PCT WO 92/1224), but even the nine-dentate chelates synthesized so far do not reach 100% quantum yield. It is well known in the literature, that the high energy vibrations of O—H and C—H stretching (vibrational manifold with harmonic overtones) play a leading role in the non-radiative energy transfer processes in the lanthanide chelates (Sinha, A. P. B., 1971, In Rao, C. N. and Ferrano J. R. (ed.), Spectroscopy in Inorganic Chemistry, Horrocks, W. DeW. and Sudnick, D. R., 1981, Acc Chem Res 14; 384–92).

SUMMARY OF THE INVENTION

According to the present invention, the problem of luminescence quenching by C—H vibrational manifolds can be solved and the development of more luminescent lanthanide chelates is made possible. By replacing hydrogen atoms with deuterium atoms in the C—H moieties the excited state deactivation route can be eliminated. The development of chelating agents containing deuterated chelating groups, e.g. deuterated iminobis(acetic acids), enable reaching of higher quantum yields, use of more stable chelates, and finally development of more sensitive bioanalytical assays.

One object of the present invention is to provide a highly luminescent lanthanide chelate as well as a method for its preparation.

Another object of this invention is to provide a detectable molecule comprising a biospecific binding reactant attached to the highly luminescent lanthanide chelate according to this invention.

A further object of this invention is to provide a chelating agent useful for the preparation of the highly luminescent lanthanide chelate according to this invention.

DETAILED DESCRIPTION OF THE INVENTION

The aim of the present invention is to provide means to obtain improved lanthanide chelate labels to be used in specific bioaffinity based binding assays, such as immunoassays, DNA hybridization assays, receptor binding assays, immunocytochemical or immunohistochemical assays utilizing fluorometric or time-resolved fluorometric determination of the specific luminescence.

The chelates of the invention have to combine several important features on a single complex, such as:
1. high absorptivity at suitable wavelength (preferable over 300 nm),
2. efficient energy transfer from UV absorbing part (triplet sensitizer) to the chelated lanthanide (III) ion,
3. strongly chelating part to create
   a) the thermodynamic stability required for storing the labelled reagents for extended periods of time and
   b) high kinetic stability to allow the use of reagents in conditions where competing metallic ions or chelating agents may be present,
4. chelating part forming as complete protection of the chelated ion as possible, preferably nine-dentate ligand,
5. functional group allowing efficient coupling of the chelate to the used binding reagent (e.g. antibody) without destroying its binding properties and decreasing the luminescent properties of the chelate.

In addition the chelate has to be highly hydrophilic and possess low nonspecific binding affinity to proteins or surfaces used in the analysis.

In one aspect therefore, the present invention provides a method to produce a highly luminescent lanthanide chelate wherein a lanthanide ion is complexed to a chelating agent, said chelating agent comprising
a chromophoric moiety comprising one or more chromophoric groups able to absorb excitation light and transfer the excited energy to the chelated lanthanide ion
at least one functional group enabling the coupling of the chelate to a biospecific binding reactant, and
a chelating part comprising one or more side chains attached to the chromophoric moiety, said chelating part comprising one or more chelating heteroatoms. The method is characterized by the use of a chelating agent in which the chelating part has carbon chains where at least part of the hydrogen atoms in the close vicinity of the lanthanide ion have been replaced by deuterium atoms.

In another aspect, this invention provides a highly luminescent lanthanide chelate comprising a lanthanide ion and a chelating ligand, said chelating ligand comprising
a chromophoric moiety comprising one or more chromophoric groups able to absorb excitation light and transfer the excited energy to the chelated lanthanide ion
at least one functional group enabling the coupling of the chelate to a biospecific binding reactant, and
a chelating part comprising one or more side chains attached to the chromophoric moiety, said chelating part comprising one or more chelating heteroatoms. The chelate is characterized in that the chelating part has carbon chains where at least part of the hydrogen atoms in the close vicinity of the lanthanide ion have been replaced by deuterium atoms.

In yet another aspect, this invention provides a detectable molecule comprising a biospecific binding reactant attached to a highly luminescent lanthanide chelate comprising a lanthanide ion and a chelating ligand, said chelating ligand comprising
a chromophoric moiety comprising one or more chromophoric groups able to absorb excitation light and transfer the excited energy to the chelated lanthanide ion
at least one functional group enabling the coupling of the chelate to a biospecific binding reactant, and
a chelating part comprising one or more side chains attached to the chromophoric moiety, said chelating part comprising one or more chelating heteroatoms. The molecule is characterized in that the chelating part has carbon chains where at least part of the hydrogen atoms in the close vicinity of the lanthanide ion have been replaced by deuterium atoms.

In yet another aspect, this invention provides a chelating agent comprising
a chromophoric moiety comprising one or more chromophoric groups able to absorb excitation light and transfer the excited energy to the chelated lanthanide ion
at least one functional group enabling the coupling of the chelate to a biospecific binding reactant, and
a chelating part comprising one or more side chains attached to the chromophoric moiety, said chelating part comprising one or more chelating heteroatoms. The chelating agent is characterized in that the chelating part has carbon chains where at least part of the hydrogen atoms coming into close vicinity of the lanthanide ion to be chelated, have been replaced by deuterium atoms.

The term "luminescent" shall in this invention be understood to mean "photoluminescent" as already stated above.

The term "hydrogen" or "H" shall be understood to mean the the $^1$H-isotope, while the term "deuterium" or "D" shall be understood to mean the $^2$H-isotope.

The term "heteroatom" means N, O or S. Preferable heteroatoms are N or O.

The term "chromophoric moiety" means the same as "excitation light absorbing moiety" which is discussed in detail below.

The terms "functional group enabling the coupling", "chelating part" and "close vicinity" are also all discussed below.

Figure 1:
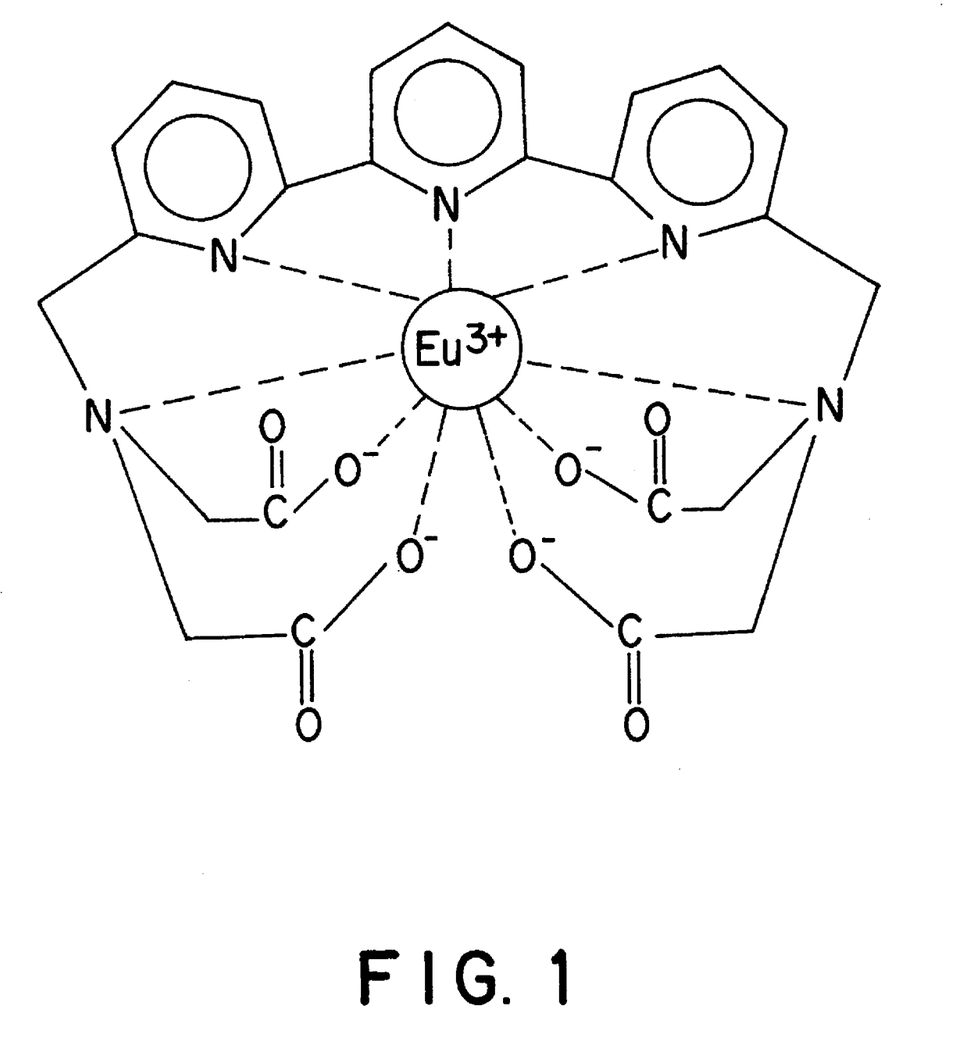
FIGURE 1 illustrates an example of chelate formation of Eu(III) with a poly-dentate chelating ligand.

Specifically according to the present invention the ligand used should not contain high energy vibrational bonds, such as O—H, C—H or N—H bonds in the near vicinity of the emittive lanthanide ion. The chelating part attached to the excitation light absorbing moiety is generally composed of polycarboxylic acid but may also be composed of phenolic groups, aromatic or aliphatic amines (preferably tertiar), polyphosphonic acid, ethylene glycol chain, it may be an open structure or form a macrocyclic closed cage-type of structure. According to the present invention, one very important feature on the chelating part is its protective effect against aqueous quenching (O—H vibrational manifolds) and the avoidance of high energy C—H vibrational oscillators in the close vicinity of the emittive ion. In close vicinity we mean those C—H bonds which are in a distance of two to three bonds apart from the emittive ion (including the coordination bond formed between the ion and the heteroatoms in the chelating parts), and are so situated directly in the 5 or 6-membered rings formed upon chelate formation as exemplified in FIG. 1. FIG. 1 illustrates an example of chelate formation of Eu(III) with a poly-dentate chelating ligand wherein the chelated ion becomes a part of 5-membered rings (8 rings in this example) including two heteroatoms of the chelating parts (in this example N and/or O). In a multi-dentate chelating ligand the excessive C—H bonds can be omitted by synthesizing the chelator using CD and $CD_2$ groups instead of CH and $CH_2$ groups.

The chelated ion is tervalent lanthanide ion which produces its typical energy-transfer based luminescence. The preferred lanthanide ions are Eu(III), Tb(III), Sm(III) or Dy(III).

The excitation light absorbing moiety in the chelating ligand (i.e. triplet sensitizer) has to be chosen so that the excitation energy absorbed is also efficiently transferred to the emittive resonance level of the chelated ion. This energy transfer generally takes place through the excited triplet level of the ligand (Sinha, 1971). The literature knows a great number of aromatic structures functioning as energy donating groups (chromophoric groups) including various pyridine derivatives, bipyridines, terpyridines, ortho- phenanthroline, coumarin derivatives, phenolic compounds and β-diketones. Examples of suitable structures can be found e.g. from the patents mentioned above, and in addition from the following articles; Toner, J. L., Lanthanide chelates as luminescent Probes, Int. Symposium of Inclusion Phenomena and Molecular Recognition, J. Atwood (ed.), Plenum Press, New York 1990, Kallistratos, K., Fluorescent properties of aromatic complexes with rare earth and other elements of the IIIa-group, Chimica Chronika, New Series, 11; 249–66, 1982, Mukkala, V.-M., Development of stable, photoluminescent europium(III) and terbium(III) chelates suitable as markers in bioaffinity assays; their synthesis and luminescence properties, Academic Dissertation, Turku, 1993.

Finally the optimally luminescent chelate has to be coupled to specific reagents by using suitable groups attached to either to the chelating part or to the excitation light absorbing moiety. The group can be selected from the group consisting of hydroxy, nitro, amino, aminooxy, carboxyl, hydroxy, aldehyde or mercapto groups or an activated form made from them, such as isocyanato, isothiocyanato, diazonium, bromoacetamido, iodoacetamido, reactive esters, pyridyl-2-dithio, 4-chloro-6-ethoxy-1,3,5-triazon-2-yl-amino or 4,6-dichloro-1,3,5-triazon-2-ylamino. The activated group should not adversely effect neither to the luminescence of the parent chelate nor reactivity of the specific binding reagent. The position of attachment in the chelate may be on the aromatic part, which has the disadvantage that modification of aromatic part, necessary for energy collection and donation, often leads to decreased luminescence. The binding group can also be attached to a side-chain in the chelating part of the molecule as mentioned in U.S. Pat. No. 5,216,134.

The invention is exemplified also with the following examples describing the effect of deuteration in sevendentate and in nine-dentate luminescent chelates and demonstrating the importance of shielding of the emittive ion against both aqueous deactivation and deactivation through C—H vibrational manifolds. Also an example of deuterated highly luminescent Eu-labeling reagent is given, the coupling of it to an antibody and the luminescence properties of labeled antibody.

The structures and the synthetic routes employed in the experimental part are shown in reaction schemes I to VIII. Scheme I illustrates the synthesis of compounds 1 to 4 exemplified by Examples 1 to 4. Scheme II illustrates the synthesis of compound 5 as described in Example 5. Scheme III illustrates the synthesis of compounds 6, 7 or 8 as described in Examples 6–9. Scheme IV illustrates the synthesis of compounds 9, 10 and 11 starting from one of the compounds 6, 7 or 8 as described in Examples 10–13. Scheme V illustrates the synthesis of compounds 12, 13, 14 and 15 starting from one of the compounds 9, 10 or 11 as described by Examples 14–18. Scheme VI illustrates the synthesis of compound 16 according to Example 19. Scheme VII illustrates the synthesis of compounds 17, 18, 19 and 20 starting from one of the compounds 12, 13, 14 or 16 as described in Examples 20–24. Scheme VIII illustrates the synthesis of compounds 21, 22, 23 and complexes 24 and 25 according to Examples 25–29.

Scheme I

Scheme II

Scheme III

5: Ar = 2,2':6',2''-terpyridine-6,6''-diyl; $R^1$ = Me
Ar = 4-bromopyridine-2,6-diyl; $R^1$ = Et 6: Ar = 2,2':6',2''-terpyridine-6,6''-diyl; $R^2$ = H
7: Ar = 2,2':6',2''-terpyridine-6,6''-diyl; $R^2$ = D
8: Ar = 4-bromopyridine-2,6-diyl; $R^2$ = D Scheme IV 9: Ar = 2,2':6',2''-terpyridine-6,6''-diyl; $R^2$ = H
10: Ar = 2,2':6',2''-terpyridine-6,6''-diyl; $R^2$ = D
11: Ar = 4-bromopyridine-2,6-diyl; $R^2$ = D Scheme V

9–11 ⟶

12: Ar = 2,2':6',2"-terpyridine-6,6"-diyl; $R^2$ = D, $R^3$ = H, $R^4$ = $^t$Bu
13: Ar = 2,2':6',2"-terpyridine-6,6"-diyl; $R^2$ = H, $R^3$ = D, $R^4$ = Me
14: Ar = 2,2':6',2"-terpyridine-6,6"-diyl; $R^2$ = $R^3$ = D, $R^4$ = Me
15: Ar = 4-bromopyridine-2,6-diyl; $R^2$ = $R^3$ = D, $R^4$ = Me Scheme VI -continued Scheme VI

Scheme VII

12–14, 16 ⟶

17: Ar = 2,2':6',2"-terpyridine-6,6"-diyl; $R^2$ = D, $R^3$ = H
18: Ar = 2,2':6',2"-terpyridine-6,6"-diyl; $R^2$ = H, $R^3$ = D
19: Ar = 2,2':6',2"-terpyridine-6,6"-diyl; $R^2$ = $R^3$ = D
20: Ar = 4-(phenylethynyl)pyridine-2,6-diyl; $R^2$ = $R^3$ = D Scheme VIII -continued
Scheme VIII

EXAMPLE 1

Bromo-[$^2$H$_2$]-acetic[$^2$H]-Acid (1)

Bromine (33.6 g, 0.21 mol) was added during 10 min into a mixture of [$^2$H$_3$]-acetic [$^2$H]-acid (11.6 g 0.18 mol) and red phosphorus (0.23 g, 7.43 mmol) at 100°–105° C. After stirring for 2 h, the product was distilled under reduced pressure: 16.4 g (64%). IR (film): 1730, 1408, 1285 (C=O, C—O).

EXAMPLE 2

Methyl Bromo-[$^2$H$_2$]-acetate (2)

SOCl$_2$ (27.27 g, 0.230 mol) was dropped slowly to cooled dry MeOH (70 ml). After stirring at r.t. for 0.5 h, 1 (16.28 g, 0.115 mol) was added, the mixture was refluxed for 6 h and evaporated nearly to dryness. The residue was dissolved in CHCl₃ (100 ml), neutralized with sat. NaHCO₃, washed with H₂O (20 ml), dried (Na₂SO₄) and the residue distilled: 3.56 g (20%). IR (film): 1760, 1438, 1261 (C=O, C—O). ¹H-NMR (CDCl₃): 3.81 (s, 3 H).

EXAMPLE 3

Methyl Amino-[²H₂]-acetate Hydrochloride (3)

SOCl₂ (2.97 g, 25.0 mmol) was dropped slowly to cooled dry MeOH (10 ml) After stirring at r.t. for 0.5 h, [²H₂]-amino-[²H₂]-acetic [²H]-acid (1.00 g, 12.5 mmol) was added, the mixture was refluxed for 18 h and evaporated to dryness. Yield: 1.60 g (100%). IR (film): 1748, 1433, 1330 (C=O, C-O). ¹H-NMR (CDCl₃): 3.73 (s, 3 H); 8.56 (broad s, 3 H).

EXAMPLE 4

Dimethyl Iminobis ([²H₂]-acetate) (4)

A mixture of 3 (1.38 g, 10.8 mmol), dry K₂CO₃ (7.46 g, 54.0 mmol) and dry MeCN (50 ml) was refluxed for 10 min, and 2 (1.68 g, 10.8 mmol) was added. After refluxing for 6.5 h, the mixture was filtered, evaporated and the product purified by FC (silica gel, petroleum ether (b.p. 40°–60° C.)/AcOEt 2:5): 1.11 g (62%). IR (film): 3355 (N—H), 1743, 1437, 1280 (C=O, C-O). ¹H-NMR (CDCl₃): 1.98 (broad s, 1H); 3.74 (s, 6 H).

EXAMPLE 5

Dimethyl 2,2':6',2"-Terpyridine-6,6"-dicarboxylate (5)

A mixture of 6,6"-dicyano-2,2':6',2"-terpyridine (2.40 g, 8.47 mmol), AcOH (25 ml) and H₂SO₄ (25 ml) was refluxed for 1.5 h. The solution was poured to ice, the precipitate was filtered, washed with H₂O and dried. The mixture of dry MeOH (150 ml) and SOCl₂ (2.0 ml) was stirred for 15 min, and 2,2':6',2"-terpyridine-6,6"-dicarboxylic acid was added. The mixture was refluxed for 5 h. The solution was evaporated to half a volume and sat. NaHCO₃ (250 ml) was added. The mixture was extracted with CHCl₃ (3×200 ml) and the CHCl₃ phase was washed with H₂O, was dried (Na₂SO₄) and evaporated: 1.95 g (66%). UV (EtOH): 3.15 (sh), 301 (sh), 288, 248, 216 nm. IR (KBr): 1724 (C=O), 1578 (arom), 1432, 1135 (C-O). ¹H-NMR (CDCl₃): 4.06 (s, 6 H); 8.02 (t, J=7.6, 2 H); 8.02 (t, J=7.6, 4 H); 8.18 (dd, J=1.0 & 7.6, 2 H); 8.63 (d, J=7.6, 2 H); 8.81 (dd, J=1.0 & 7.6, 2 H).

EXAMPLE 6

Synthesis of 6–8: General Procedure

A mixture of 5 or diethyl 4-bromopyridine-2,6-dicarboxylate (6.23 mmol), abs. EtOH (80 ml) and NaBH₄ or NaBD₄ (28.0 mmol) was refluxed for 3–20 h. The solvent was evaporated, sat. NaHCO₃ (40 ml) was added and the mixture was heated to boiling. H₂O (120 ml) was added, the mixture was cooled to 0° C and filtered.

EXAMPLE 7

(2,2':6',2"-Terpyridine-6,6"-diyl)dimethanol (6)

Yield: 58%. UV (EtOH): 315 (sh), 301 (sh), 286, 239 nm. IR (KBr): 3415 (O—H), 1571 (arom). ¹H-NMR ((D₆)-DMSO): 4.70 (s, 4 H); 5.56 (s, 2 H); 7.58 (d, J=7.7, 2 H); 8.02 (t, J=7.7, 2 H); 8.09 (t, J=7.7, 1 H); 8.43 (d, J=7.7, 2 H); 8.49 (d, J=7.7, 2 H).

EXAMPLE 8

(2,2':6',2"-Terpyridine-6,6"-diyl)di-[²H₂]-methanol (7)

Yield: 63%. UV (EtOH): 315 (sh), 302 (sh), 286, 239 nm. IR (KBr): 3417 (O—H), 1576 (arom). ¹H-NMR ((D₆)-DMSO): 5.50 (s, 2 H); 7.58 (dd, J=1.0 & 7.8, 2 H); 8.01 (t, J=7.8, 2 H); 8.08 (t, J=7.8, 1 H); 8.43 (d, J=7.8, 2 H); 8.49 (dd, J=1.0 & 7.8, 2 H).

EXAMPLE 9

(4-Bromopyridine-2 6-diyl)di-[²H₂]-methanol (8)

After addition of H₂O, the mixture was extracted with CHCl₃/EtOH (2:1, 3×15 ml) and dried (NaSO₄). Yield: 84%. UV (EtOH): 272, 265 nm. IR (film): 3355 (O—H), 1579 (arom.). ¹H-NMR ((D₆)DMSO): 5.51 (s, 2 H); 7.52 (s, 2 H).

EXAMPLE 10

Synthesis of 9–11: General Procedure

A sol. of PBr₃ (0.42 g, 1.55 mmol) and CHCl₃ (3.5 ml) was added to a suspension of the respective compound 6–8 (1.03 mmol) and the mixture was refluxed for 4 h, neutralized with 5% NaHCO₃ and aq. phase was extracted with CHCl₃ (5×10 ml). The CHCl₃ phase was dried (NASO₄) and the product purified by FC (silica gel).

EXAMPLE 11

6,6"-Bis(bromomethyl)-2,2':6',2"-terpyridine (9)

Yield: 50%. UV (EtOH): 315 (sh), 302 (sh), 289, 245 nm. IR (KBr): 1575, 1566 (arom). ¹H-NMR (CDCl₃): 4.66 (s, 4 H); 7.49 (dd, J=0.7 & 7.7, 2 H); 7.86 (t, J=7.7, 2 H); 7.96 (t, J=7.7, 1 H); 8.52 (d, J=7.7, 2 H); 8.53 (dd, J= 0.7 & 7.7, 2 H).

EXAMPLE 12

6,6"-Bis ([²H₂]-bromomethyl)-2,2':6',2"-terpyridine (10)

Yield: 59%.UV (EtOH): 315 (sh), 302 (sh), 288, 246 nm. IR (KBr): 1576, 1567 (arom). ¹H-NMR (CDCl₃): 7.49 (d, J=7.8, 2 H); 7.86 (t, J=7.8, 2 H); 7.96 (t, J=7.8, 1 H); 8.52 (d, J=7.8, 2 H); 8.53 (d, J=7.8, 2 H).

EXAMPLE 13

4-Bromo-2,6-bis ([²H₂]-bromomethyl)pyridine (11)

FC: petroleum ether (40°–60° C.)/AcOEt 10:1. Yield: 58%. UV (EtOH): 274 nm. IR (film): 1556 (arom.). ¹H-NMR (CDCl₃): 7.55 (s, 2 H).

EXAMPLE 14

Synthesis of 12–15: General Procedure

A mixture of the respective compound 9–11 (0.57 mmol), 4 or di(tert-butyl) iminobis (acetate) (1.15 mmol ), dry $K_2CO_3$ and dry MeCN (10 ml) was stirred for 24 h at r.t. After filtration and evaporation, the product was purified by FC (silica gel).

EXAMPLE 15

Tetra (tert-butyl) 2,2',2",2"'-[(2,2':6',2"-Terpyridine-6,6"-diyl )bis([$^2H_2$]-methylenenitrilo)]tetrakis (acetate) (12)

FC: $CHCl_3$/MeOH 19:1. Yield: 73%. UV (EtOH): 316 (sh), 302 (sh), 284, 233 nm. IR (KBr): 1738 (C=O), 1570 (arom), 1433, 1148 (C-O). $^1$H-NMR ($CDCl_3$): 1.47 (s, 36 H); 3.55 (s, 8 H); 7.65 (d, J=7.8 Hz, 2 H); 7.84 (t, J=7.8 Hz, 2 H); 7.90 (t, J=7.8 Hz, 1 H); 8.47 (d, J=7.8 Hz, 2 H); 8.49 (d, J=7.8 Hz, 2H).

EXAMPLE 16

Tetramethyl 2,2',2",2"'-[(2,2':6',2"-Terpyridine-6,6"-diyl)bis(methylenenitrilo)]tetrakis ([$^2H_2$]-acetate) (13)

FC: $CHCl_3$/MeOH 19:1. Yield: 44%. UV (EtOH): 317 (sh), 304 (sh), 283, 228 nm. IR (KBr): 1746 (C=O), 1569 (arom), 1433, 1170 (C-O). $^1$H-NMR ($CDCl_3$): 3.72 (s, 12 H); 4.16 (s, 4 H); 7.58 (d, J=7.8 Hz, 2 H); 7.84 (t, J=7.8 Hz, 2 H); 7.92 (t, J=7.8 Hz, 1 H); 8.45 (d, J=7.8 Hz, 2 H); 8.50 (d, J=7.8 Hz, 2 H).

EXAMPLE 17

Tetramethyl 2,2',2",2"'-[(2,2':6',2"-Terpyridine-6,6"-diyl)bis([$^2H_2$]-methylenenitrilo)]tetrakis([$^2H_2$]-acetate) (14)

FC: $CHCl_3$/MeOH 19:1. Yield: 54%. UV (EtOH): 315 (sh), 303 (sh), 284, 231 nm. IR (KBr): 1748 (C=O), 1569 (arom), 1434, 1212 (C-O). $^1$H-NMR ($CDCl_3$): 3.72 (s, 12 H); 7.58 (dd, J= 1.0 & 7.8 Hz, 2 H); 7.85 (t, J=7.8 Hz, 2 H); 7.93 (t, J= 7.8 Hz, 1 H); 8.45 (d, J=7.8 Hz, 2 H); 8.51 (dd, J=1.0 & 7.8Hz, 2H).

EXAMPLE 18

Tetramethyl 2,2',2",2"'-[(4-Bromopyridine-2,6-diyl) bis ([$^2H_2$ ]-methylenenitrilo)]tetrakis ([$^2H_2$]-acetate) (15)

FC: petroleum ether (40°–60° C.)/AcOEt 1:1. Yield 48%. UV (EtOH): 260 nm. IR (film): 1745 (C=O), 1563 (arom), 1436, 1221 (C-O). $^1$H-NMR ($CDCl_3$): 3.71 (s, 12 H); 7.72 (s, 2 H).

EXAMPLE 19

Tetramethyl 2,2',2",2"'-{[4-(Phenylethynyl)pyridine-2,6-diyl]bis([$^2H_2$]-methylenenitrilo)}tetrakis ([$^2H_2$]-acetate) (16)

A mixture of 15 (62 mg, 0.12 mmol), bis(triphenylphosphine)palladium(II) chloride (2.5 mg, 3.6 μmol), and CuI (1.4 mg, 7.2 μmol) in dry $Et_3N$ (0.9 ml) and dry THF (0.9 ml) was deaerated with $N_2$. Phenylacetylene (21 mg, 0.21 mmol) was added and the mixture was heated at 50° C. for 24 h. After evaporation, the product was purified by FC (silica gel, first petroleum ether (40°–60° C.)/AcOEt 1:1, then AcOEt). Yield: 50 mg (77%). UV (EtOH): 302 (sh), 281, 270 (sh), 245, 238 (sh), 224 (sh) nm. IR (film): 2216 (C≡C), 1749 (C=O), 1590 (arom.), 1422, 1216 (C-O). $^1$H-NMR ($CDCl_3$): 3.72 (s, 12 H); 7.31–7.42 (m, 3 H); 7.54 (d, J=3.4, 2 H); 7.56 (s, 2 H).

EXAMPLE 20

2,2',2",2"'-[(2,2':6',2"-Terpyridine-6,6"-diyl)bis([$^2H_2$]-methylenenitrilo)]tetrakis(acetic Acid) (17)

A sol. of 12 (74 mg, 0.099 mmol) in $CF_3COOH$ (4 ml) was stirred for 2.5 h at r.t. After evaporation, the mixture was triturated with $Et_2O$ and filtered. Yield: 100%. UV ($H_2O$): 288, 233 nm. UV ([$Eu^{III}$(17)], $H_2O$): 337, 326, 292, 284, 235 nm. IR (KBr): 1734 (C=O), 1570 (arom), 1436, 1195 (C-O). $^1$H-NMR (($D_6$)-DMSO): 3.75 (s, 8 H); 7.66 (d, J=7.8, 2 H); 8.05 (t, J=7.8, 2 H); 8.12 (t, J=7.8, 1 H); 8.45 (d, J=7.8, 2 H); 8.56 (d, J=7.8, 2 H).

EXAMPLE 21

Synthesis of 18–20: General Procedure

A mixture of 13, 14 or 16 (0.087 mmol), 0.5M KOH/EtOH (3.2 ml), $H_2O$ (0.5 ml) was stirred for 2.5–4 h at r.t., evaporated, dissolved in $H_2O$ (5 ml) and acidified with 2M HCl (pH ca. 2.0). The precipitate was filtered and washed with cold $H_2O$.

EXAMPLE 22

2,2',2",2"'-[(2,2':6',2"-Terpyridine-6,6"-diyl)bis(methylenenitrilo)] tetrakis ([$^2H_2$]-acetic Acid) (18)

UV ($H_2O$): 292, 234 nm. UV ([$Eu^{III}$(18)], $H_2O$): 337, 326, 292, 282, 235 nm. IR (KBr): 1728, 1628 (C=O), 1570 (arom), 1436, 1267 (C-O). $^1$H-NMR (($D_6$)DMSO): 4.11 (s, 4 H); 7.63 (d, J= 7.6, 2 H); 8.01 (t, J=7.6, 2 H); 8.09 (t, J=7.6, 1 H); 8.42 (d, J=7.6, 2 H); 8.50 (d, J=7.6, 2 H).

EXAMPLE 23

2,2',2",2"'-[(2,2':6',2"-Terpyridine-6,6"-diyl) bis([$^2H_2$]-methylenenitrilo)]tetrakis([$^2H_2$]-acetic Acid) (19)

UV ($H_2O$): 288, 230 nm. UV ([$Eu^{III}$(19)], $H_2O$): 337, 326, 292, 283, 235 nm. IR (KBr): 1727, 1628 (C=O), 1570 (arom), 1436, 1274 (C-O). $^1$H-NMR (($D_6$)DMSO): 7.63 (d, J=7.8, 2 H); 8.02 (t, J=7.8, 2 H); 8.10 (t, J=7.8, 1 H); 8,43 (d, J= 7.8, 2 H); 8.52 (d, J=7.8, 2 H).

EXAMPLE 24

2,2',2'',2'''-{[4-(Phenylethynyl)pyridine-2,6-diyl]bis([$^2$H$_2$]-methylenenitrilo)}tetrakis ([$^2$H$_2$]-acetic Acid ) (20)

UV (H$_2$O): 313 (sh), 276, 245 (sh) nm. UV ([Eu$^{III}$(20)], H$_2$O): 317 (sh), 273, 260 (sh), 245 (sh) nm. IR (KBr): 2216 (C≡C), 1728 (C=O), 1605 (C-N), 1273 (C-O). $^1$H-NMR ((D$_6$)DMSO): 7.45–7.50 (m, 3 H); 7.57 (s, 2 H); 7.63 (d, J=5.7, 2 H).

EXAMPLE 25

Tetramethyl 2,2',2'',2'''-{[4'-(4'''-Nitrophenyl)-2,2':6',2''-terpyridine-6,6''-diyl]bis(methylenenitrilo)}tetrakis([$^2$H$_2$]-acetic Acid) (21)

A mixture of [4'-(4'''-nitrophenyl)-2,2':6',2''-terpyridine-6,6''-diyl]bis(methylamine)×5 HCl (0.47 g, 0.79 mmol), BrCD$_2$COOMe (0.49 g, 3.16 mmol), dry (i-Pr)$_2$EtN (1.53 g, 11.9 mmol), and dry MeCN (20 ml) was refluxed for 20 h. After evaporation, the residue was dissolved in CHCl$_3$ (50 ml), the soln. washed with H$_2$O (3×20 ml) and dried (Na$_2$SO$_4$), and the product purified by FC (siliga gel, petroleum ether (40°–60° C.)/AcOEt/Et$_3$N 5:3:1). Yield 0.10 g (18%). UV (EtOH): 286, 255, 246 nm. IR (KBr): 1746 (C=O), 1581 (arom), 1519 (N-O), 1435 (C-O), 1349 (N-O), 1255 (C-O). $^1$H-NMR (CDCl$_3$): 3.70 (s, 12 H); 4.19 (s, 4 H); 7.63 (d, J=7.6, 2 H); 7.89 (t, J=7.6, 2 H); 8.09 (d, J=8.8, 2 H); 8.41 (d, J=8.8, 2 H); 8.56 (d, J=7.6, 2 H); 8.75 (s, 2 s).

EXAMPLE 26

Tetramethyl 2,2',2'',2'''-{[4'-(4'''-Aminophenyl)-2,2':6',2''-terpyridine-6,6''-diyl]bis(methylenenitrilo)}tetrakis ([$^2$H$_2$]-acetic Acid) (22)

SnCl$_2$.2H$_2$O (0.16 mmol, 0.71 mmol) was added to a hot (70°– 80° C.) soln. of 21 (0.10 g, 0.14 mmol) in abs EtOH (5 ml). After stirring at 70°–80° C. for 45 min, the cooled mixture was poured to an ice-cold mixture of DTPA (1.10 g, 2.80 mmol) and H$_2$O (20 ml). The mixture was neutralized with sat. NaHCO$_3$ soln., the aq. phase extracted with CHCl$_3$ (3×15 ml), and the combined org. phase dried (Na$_2$SO$_4$). Yield 0.91 g (96%). UV (EtOH): 325 (sh), 300 (sh), 288, 254, 232 nm. IR (KBr): 1744 (C=O), 1580 (arom), 1435, 1259 (C-O). $^1$H-NMR (CDCl$_3$): 3.70 (s, 12 H); 4.18 (s, 4 H); 6.83 (d, J=8.3, 2 H); 7.57 (d, J=7.8, 2 H); 7.77 (d, J=8.3, 2 H); 7.85 (t, J=7.8, 2 H); 8.53 (d, J=7.8, 2 H); 8.67 (s, 2 H).

EXAMPLE 27

2,2',2'',2'''-{[4'-(4'''-Aminophenyl)-2,2':6',2''-terpyridine-6,6''-diyl]bis(methylenenitrilo)}tetrakis ([$^2$H$_2$]-acetic Acid) (23)

The compound 23 was prepared from 22 analogously to 18–20. Yield: 74%. UV (H$_2$O): 322, 303 (sh), 286, 245, 232 nm. IR (KBr): 1727, 1627 (C=O), 1587 (arom), 1395, 1267 (C-O). $^1$H NMR ((D$_6$)DMSO): 4.22 (s, 4 H); 6.78 (d, J=8.8, 2 H); 7.65 (d, J=7.6, 2 H); 7.73 (d, J=8.8, 2 H); 8.05 (t, J=7.6, 2 H); 8.56 (d, J=7.6, 2 H); 8.63 (s, 2 H).

EXAMPLE 28

{2,2',2'',2'''-{[4'-(4'''-Aminophenyl)-2,2':6',2''-terpyridine-6,6''-diyl]bis(methylenenitrilo)}tetrakis ([$^2$H$_2$]acetato)} europium(III) (24)

Tetraacid 23 (31 mg, 50 μmol) was dissolved in H$_2$O (0.8 ml) and the pH adjusted to 6.5 with solid NaHCO$_3$. EuCl$_3$ (21 mg, 58 μmol) in H$_2$O (0.4 ml) was added during 15 min and the pH maintained at 5–7. After stirring for 1.5 h, the pH was raised to 8.5 with 1M NaOH, the precipitate filtered off, the filtrate treated with acetone, and the precipitate filtered and washed with acetone. The product was used in the next step without further purification. UV (H$_2$O): 329, 294, 272 (sh), 237 nm. IR (KBr): 1598 (C=O), 1399 (C-O).

EXAMPLE 29

{2,2',2'',2'''-{{4'-{4'''-[(4,6-Dichloro-1,3,5-triazin-2-yl)amino]phenyl}-2,2':6',2''-terpyridine-6,6''-diyl}bis(methylenenitrilo)}tetrakis([$^2$H$_2$]-acetato)}europium(III) (25)

A mixture of 2,4,6-trichloro-1,3,5-triazine (9.2 mg, 50 μmol), acetone (0.5 ml), and H$_2$O (0.5 ml) was added to a soln. of amino chelate 24 (50 μmol) and 0.1M NaOAc (0.75 ml, pH 4.9). After stirring for 30 min, acetone was added to the mixture and the product 25 (27 mg, 55%) filtered and washed with acetone. UV (H$_2$O): 350 (sh), 288, 233 (sh) nm. IR (KBr): 1602, 1398, 1227 (C=O, C-O).

EXAMPLE 30

Luminescence properties of deuterated compound (20) as compared to the respective undeuterated compound The effect of deuteration was first tested with a sevendentate phenylethynylpyridine derivative (20) both as Tb and as Eu chelates. The parameters obtained in aqueous buffer and in deuterium oxide are presented in Table 1 below and compared to the results obtained from an undeuterated chelate synthesized earlier (U.S. Pat. No. 4,920,195). The experiment clearly demonstrates the importance of ion protection both against O—H quenching and against C—H quenching. However, because the energy leakage through O—H vibrational energy levels is more strong, the positive effect of deuterium substitution can only be found in deuterium oxide showed both as an increased total luminescence intensity and the prolonged decay time. Because the energy cap, the cap between the lowest excited resonance level and the highest level of the ground state manifold, is larger with Tb(III) (about 14,650 cm$^{-1}$) as compared to Eu(III) (about 12,300 cm$^{-1}$), the vibrational manifold of C—H is not as strong excited state relaxing route with Tb(III) as it is with Eu(III).

EXAMPLE 31

The effect of deuteration level on luminescence of stable Eu(III) chelate

The effect of substitution of hydrogens with deuteriums in a nine-dentate chelating agents (17, 18 and 19) was studied in an aqueous solution by measuring their luminescence parameters as Eu(III) chelates as compared to the respective undeuterated analogue (U.S. Pat. No. 5,202,423). These chelating agents, which as nine-dentate ligands fulfill the primary criterion, i.e. the efficient ion shielding from the quenching water molecules, reveale the energy leakage route through the high-energy C—H vibrational manifolds. Both the decay times (from 1260 to 1610 µs) and the relative luminescence intensities (from 940 to 1470) increased by increasing the deuteration level from zero to 12 as shown in Table 2 below.

EXAMPLE 32

Coupling of Eu(III) complex of a deuterated ligand (25) with an antibody

Chelate (25) was coupled to an antibody (anti-mouse IgG) by incubating 1 mg of IgG in carbonate buffer, pH 9.3, with 30-fold molar excess of the chelate over night at 4° C. The labelled monomeric IgG was purified using a gel filtration (Sepharose 6B) by eluting with tris-HCl buffer, pH 7.5. The labelled IgG fraction was pooled, and the chelate concentration on the protein measured using a dissociative fluorescence enhancement (DELFIA). The labelling yield was 13 Eu/IgG, the relative fluorescence intensity ($\epsilon \times \Phi$) 2360 and the decay time 1600 µs. The binding properties of the labelled antibodies were further tested by measuring mouse IgG binding to plastic surfaces (microtitration strip wells) using the conjugate as a tracer.

It will be appreciated that the methods and compositions of the present invention can be incorporated in the form of a variety of embodiments, only a few of which are disclosed herein. It will be apparent to the artisan that other embodiments exist and do not depart from the spirit of the invention. Thus, the described embodiments are illustrative and should not be construed as restrictive.

TABLE 1

| Parameters | $Ln^{3+}$ | Deuterated form (20) | | Undeuterated | |
| --- | --- | --- | --- | --- | --- |
| | | $H_2O$ | $D_2O$ | $H_2O$ | $D_2O$ |
| Excitation max. (nm) | $Eu^{3+}$ | 299 | 306 | 300 | 309 |
| | $Tb^{3+}$ | 300 | 299 | 300 | 299 |
| Emission max. (nm) | $Eu^{3+}$ | 614 | 614 | 614 | 614 |
| | $Tb^{3+}$ | 544 | 544 | 544 | 544 |
| Decay-time (µs) | $Eu^{3+}$ | 400 | 2620 | 390 | 2210 |
| Intensity ($\epsilon \times \Phi$) | $Eu^{3+}$ | 263 | 3790 | 658 | 2790 |
| | $Tb^{3+}$ | 1180 | 1530 | 1160 | 1570 |

TABLE 2

| Deuteration level | Decay time, µs | Molar absorption coefficient | Luminescence intensity, $\epsilon \times \Phi$ |
| --- | --- | --- | --- |
| 0 | 1260 | 8600 | 940 |
| 4 (17) | 1500 | 8390 | 1120 |
| 8 (18) | 1480 | 9680 | 1230 |
| 12 (19) | 1610 | 9800 | 1470 |

We claim:

1. A method for producing a luminescent lanthanide chelate comprising complexing a lanthanide ion to a chelating agent, said chelating agent comprising a chromophoric moiety comprising one or more chromophoric groups able to absorb excitation light and transfer the excited energy to the chelated lanthanide ion at least one functional group enabling the coupling of the chelate to a biospecific binding reactant, and a chelating part comprising one or more side chains attached to the chromophoric moiety, said chelating part comprising one or more chelating heteroatoms and having C—H groups where at least part of the hydrogen atoms within two to three bonds of the lanthanide ion, including the coordination bond between said ion and a heteroatom, have been replaced by deuterium atoms.

2. The method according to claim 1 wherein part or all of the hydrogen atoms in the C—H groups in 5 or 6 membered chelate rings, formed together with the chelated lanthanide ion and two heteroatoms of the chelating parts, have been replaced by deuterium atoms.

3. The method according to claim 1 in which said lanthanide ion is selected from the group consisting of Eu(III), Tb(III), Sm(III) and Dy(III).

4. A luminescent lanthanide chelate comprising a lanthanide ion and a chelating ligand, said chelating ligand comprising a chromophoric moiety comprising one or more chromophoric groups able to absorb excitation light and transfer the excited energy to the chelated lanthanide ion at least one functional group enabling the coupling of the chelate to a biospecific binding reactant, and a chelating part comprising one or more side chains attached to the chromophoric moiety, said chelating part comprising one or more chelating heteroatoms and having C—H groups where at least part of the hydrogen atoms within two to three bonds of the lanthanide ion, including the coordination bond between said ion and a heteroatom, have been replaced by deuterium atoms.

5. The lanthanide chelate according to claim 4 wherein part or all of the hydrogen atoms in the C—H groups in 5 or 6 membered chelate rings, formed together with the chelated lanthanide ion and two heteroatoms of the chelating parts, have been replaced by deuterium atoms.

6. The lanthanide chelate according to claim 4 in which said lanthanide ion is selected from the group consisting of Eu(III), Tb(III), Sm(III) and Dy(III).

7. A detectable molecule comprising a biospecific binding reactant attached to a highly luminescent lanthanide chelate comprising a lanthanide ion and a chelating ligand, said chelating ligand comprising a chromophoric moiety comprising one or more chromophoric groups able to absorb excitation light and transfer the excited energy to the chelated lanthanide ion at least on functional group enabling the coupling of the chelate to a biospecific binding reactant, and a chelating part comprising one or more side chains attached to the chromophoric moiety, said chelating part comprising one or more chelating heteroatoms and having C—H groups where at least part of the hydrogen atoms within two to three bonds of the lanthanide ion, including the coordination bond between said ion and a heteroatom, have been replaced by deuterium atoms.

8. The detectable molecule according to claim 7 wherein part or all of the hydrogen atoms in the C—H groups in 5 or 6 membered chelate rings, formed together with the chelated lanthanide ion and two heteroatoms of the chelating parts, have been replaced by deuterium atoms.

9. The detectable molecule according to claim 7 in which said lanthanide ion is selected from the group consisting of Eu(III), Tb(III), Sm(III) and Dy(III).

10. The detectable molecule according to claim 7 in which said biospecific binding reactant is selected from a group consisting an antibody, antigen, receptor ligand, a specific binding protein, and a DNA- or RNA-probe.

* * * * *